United States Patent [19]

Okada

[11] Patent Number: 4,638,802
[45] Date of Patent: Jan. 27, 1987

[54] HIGH FREQUENCY INSTRUMENT FOR INCISION AND EXCISION

[75] Inventor: Tsutomu Okada, Hachioji, Japan

[73] Assignee: Olympus Optical Co., Ltd., Japan

[21] Appl. No.: 773,053

[22] Filed: Sep. 6, 1985

[30] Foreign Application Priority Data

Sep. 21, 1984 [JP] Japan .................................. 59-198053

[51] Int. Cl.⁴ ............................................. A61B 17/36
[52] U.S. Cl. .......................... 128/303.14; 128/303.17; 128/303.15
[58] Field of Search ............ 128/303.1, 303.13–303.19

[56] References Cited

U.S. PATENT DOCUMENTS 3,955,578  5/1976  Chamness et al. ............... 128/303.15

FOREIGN PATENT DOCUMENTS 3220940 12/1983  Fed. Rep. of Germany ......................... 128/303.14

OTHER PUBLICATIONS

Japanese Laid Open Patent Publication Sho 58/1983-78655 (May 12, 1983).

Primary Examiner—Kyle L. Howell
Assistant Examiner—Randy Citrin
Attorney, Agent, or Firm—Ostrolenk, Faber, Gerb & Soffen

[57] ABSTRACT

A high frequency instrument for incision and excision of the tissue of an affected part by a semi-circular loop formed by the distal end of a wire electrode upon passage of high frequency current therethrough is disclosed. The wire electrode is disposed within an electrically insulating sheath so as to be movable therein, and may be advanced or retracted by operating a proximate and operating unit. Only the advancing and retracting movement of the operating unit and the operating pipe are transmitted to the wire electrode while rotation of the operating unit and the operating pipe is not transmitted to the semi-circular loop of the wire electrode, thus preventing the loop from becoming entangled with the tissue of an affected part.

11 Claims, 8 Drawing Figures

HIGH FREQUENCY INSTRUMENT FOR INCISION AND EXCISION

BACKGROUND OF THE INVENTION

The invention relates to a high frequency instrument for incision and excision, and more particularly, to an instrument commonly referred to as a high frequency snare, high frequency knife or the like used to treat an affected part within a coeloma and which can be inserted into the coeloma to excise an affected part such as a polyp by cautery with high frequency current.

When it is required to effect excision of the tissues of an affected part which is located within the coeloma of a living body, for example, a polyp on the wall of the stomach, a high frequency instrument for incision and excision is inserted into the stomach together with an endoscope. The instrument is then moved close to the polyp and a loop which is formed on the distal end of a wire electrode of the instrument is caused to tightly bound the polyp. By passing high frequency current through the wire electrode, the polyp can be excised by cautery while observing it through the endoscope.

FIG. 1 shows one form of a conventional high frequency instrument for incision and excision. Specifically, the instrument includes a sheath 1 through which a wire electrode 3 is passed. The instrument is operated by an operating unit 2 which is mounted on the sheath 1 at the proximate end thereof. The sheath 1 and the wire electrode 3 are mounted on the operating unit so that the unit 2 cannot be rotated relative to the sheath 1 and the wire electrode 3. However, difficulties are experienced in that after mounting the operating unit 2 on the sheath, the unit 2 may be rotated. Such rotation is transmitted to the distal end through the wire electrode 3, whereby the semi-circular loop 4 located at the distal end can be twisted and become entangled around the affected part. Such difficulties can be overcome, for example, by providing as shown in FIG. 2, a fixture 5 which is connected to the proximate end of the wire electrode 3 and which is rotatable relative to the latter. Such a device is disclosed in Japanese Laid-Open Patent Application No. 78,655/1983. However, this results in the disadvantage that the semi-circular loop is again twisted and entangled with the affected part if the operating pipe 6 is rotated while the operating unit 2 is not mounted on the sheath 1. Such entangling prevents the tissue portion which is subjected to the cautery from being tightly bound in a reliable manner, and the passage of high frequency current cannot positively disconnect the tissue at the desired location. This causes the wire electrode to be seized with the tissue.

SUMMARY OF THE INVENTION

It is an object of the invention to provide a high frequency instrument for incision and excision which enables incision and excision by the use of high frequency current to be performed in a safe manner while avoiding the entangling of a loop on the wire electrode with the tissue of an affected part if the operating unit is rotated or if the operating pipe is rotated while the unit is dismounted.

In accordance with the invention, an operating pipe and a fixture which is used to connect the operating pipe to a slider of an operating unit are disposed independently from a wire electrode which has a loop formed at the distal end thereof. An arrangement is made such that an operative connection therebetween is only established during a normal operation when the wire electrode is to be advanced or retracted. In this manner, it is possible to prevent twisting of the operating unit or twisting which results from the intentional rotation of the operating pipe, from being transmitted to the distal end of the wire electrode so as to cause the loop thereon to be entangled with the affected part. The present invention provides a high frequency instrument for incision and excision which is free from the described disadvantages of the prior art while enabling reliable incision and excision of the tissue of an affected part at a desired location.

DESCRIPTION OF PREFERRED EMBODIMENTS

Figure 1:
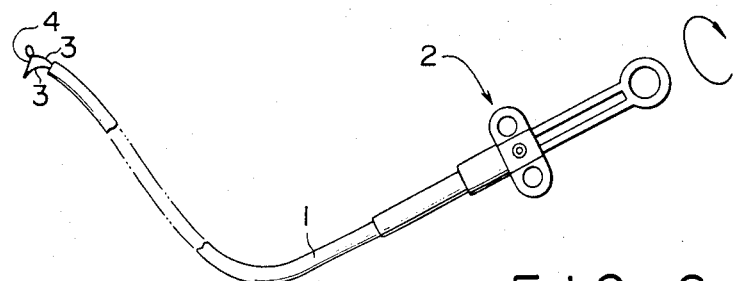
FIGS. 1 and 2 are a perspective view and a fragmentary perspective view of two forms of high frequency instruments for incision and excision as taught by the prior art.
Figure 2:
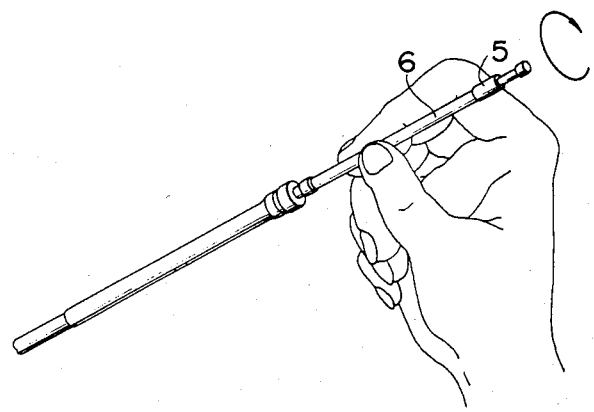
Figure 3:
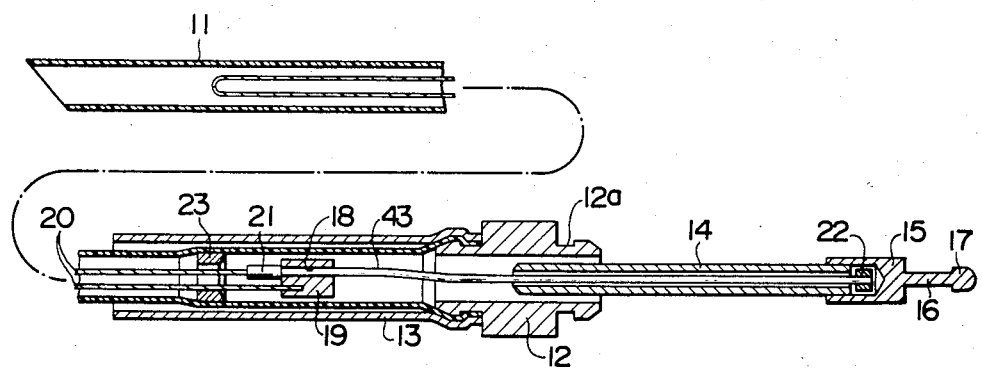
FIG. 3 is an enlarged longitudinal section of a high frequency instrument for incision and excision according to one embodiment of the invention.

Referring to FIG. 3, there is shown a high frequency instrument for incision and excision constructed according to a first embodiment of the invention wherein the operating unit is removed so as to illustrate its internal construction. This instrument is of a type which is commonly referred to as a high frequency snare. It comprises a sheath 11 formed by a cylindrical pipe of a substantial length of a flexible, electrically insulating material, having a proximate end opening to which a mouthpiece 12 formed by a hollow sleeve of a reduced length is fitted and secured. The mouthpiece 12 is detachably mounted in a chuck 29 of operating unit 25, (FIG. 4) and which will be described below. A folded-on pipe 13, which covers the proximate end of the sheath 11, is secured over the mouthpiece 12. The inner end of an operating pipe 14 is disposed within the mouthpiece 12. The pipe 14 includes an outer end projecting out of the mouthpiece 12 around which a fixture 15 is secured. The fixture 15 serves to connect the operating pipe 14 to a slider 28 (see FIG. 4) of the operating unit 25. As best shown in FIG. 3, the fixture 15 includes a rod shaped projection whose diameter is slightly greater than that of the projection 16. The rod shaped projection 16 is adapted to be detachably mounted in a retainer 31 (FIG. 4) of the slider 28.

A wire detent member 19 is disposed within the sheath 11 and is longitudinally movable therein. Member 19 includes an opening 18 extending therethrough with pipe 43 having a reduced diameter (described below) passes through. One end of a wire electrode 20 is connected to the detent member 19. The wire electrode 20 has its one end secured to the detent member 19 and extends within the sheath 11 to a point adjacent to the distal end thereof, and is then folded back to extend through the sheath 11 in the opposite direction. A retracting member 21 is then mounted on the folded-back portion of the wire electrode 20, with the wire electrode then extending through the pipe 43 so as to have its other end projecting into an internal space within the fixture 15. The inner end of the pipe 43 is force fit in the opening 18 of the detent member 19 while the outer end extends through the operating pipe 14 and projects into the internal space within the fixture 15. Therefore, the other end of the wire electrode 20, as described, extends through the opening 18 and the operating pipe 14, and projects into the internal space within the fixture 15, where it is secured at the outer end of the pipe 43 and fixedly connected to a stop 22 which is located within the internal space. The stop 22 has an outer diameter which is greater than the inner diameter of the operating pipe 14 so that it cannot extend through the operating pipe 14. When the fixture 15 is moved toward the sheath 11, the stop 22 is urged by the fixture 15 to allow the pipe 43 and hence its connected wire electrode 20 to move in the forward direction. In this manner, the operating pipe 14 is rotatable relative to the wire electrode 20 which has its other end secured to the pipe 43. Since the operating pipe 14 is integral with the fixture 15, the fixture 15 is also rotatable relative to the wire electrode 20. A detent ring 23 is secured within the sheath 11 at a location which is forward of the wire detent member 19 for abutment by the detent member 19 as it moves forward.

Figure 4:
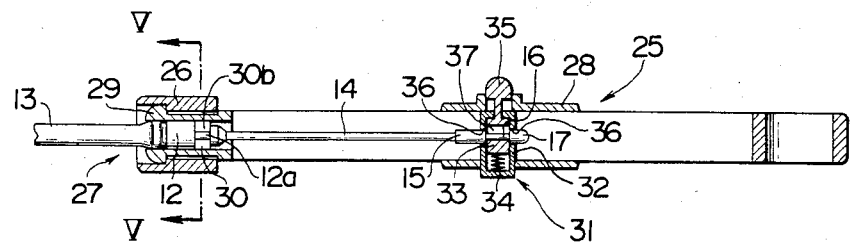
FIG. 4 is a longitudinal section of an operating unit in which the high frequency instrument of FIG. 3 is mounted.

FIG. 4 shows the operating unit 25 of the high frequency instrument thus constructed. Specifically, the unit 25 includes a receiver 27 for the mouthpiece 12 which is located at a front end thereof, and an operating slider 28 intermediate its length which is used to cause sliding movement of the fixture 15. The receiver 27 comprises a chuck 29 which rotatably receives the mouthpiece 12, a rotary ring 26 which is used to open or close the chuck 29, and a locking arrangement (described below) for the mouthpiece 12. The rotary ring 26 which is disposed around the periphery of the chuck 29, and may be rotated in one direction so that the chuck 29 can be opened, thereby allowing the mouthpiece 12 to be easily fitted into the chuck 29. When the ring 26 is rotated in the opposite direction, the chuck 29 is closed, thus allowing the mouthpiece 12 to be rotatably retained therein. In this manner, the chuck 29 allows the mouthpiece 12 of the sheath 11 to be rotatably carried therein without any rattling.

Figure 5:
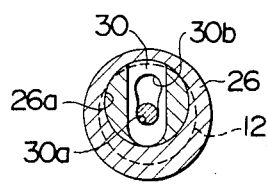
FIG. 5 is an enlarged cross section taken along the line V—V shown in FIG. 4.

Referring to FIGS. 4 and 5, it can be seen that the locking arrangement for the mouthpiece 12 comprises a slidable piece 30 which is disposed inside the rotary ring 26 in a direction perpendicular to the center axis of the sheath. A cam surface 26a is eccentrically formed around the inner periphery of the rotary ring 26, against which the opposite ends of the slidable piece 30 abut. As the rotary ring 26 is rotated in the manner mentioned above, the slidable piece 30 is displaced in a direction perpendicular to the length of the sheath 11. The slidable piece 30 is formed with a pair of openings 30a, 30b of a small diameter and an increased diameter, respectively, which are contiguous with each other in the direction of displacement of the slidable piece 30. The reduced diameter opening 30a has an inner diameter which corresponds to the outer diameter of a portion 12a (FIG. 3) of the mouthpiece 12. The increased diameter opening 30b has an inner diameter which corresponds to the outer diameter of the outer end of the mouthpiece 12.

As the rotary ring 26 is turned to close the chuck 29 so as to clamp the mouthpiece 12, the cam surface 26a causes the slidable piece 30 to be displaced to the position shown in FIG. 5. The reduced diameter portion 12a of the mouthpiece 12 is fitted into the reduced diameter opening 30a, whereby the mouthpiece 12 may be locked against disengagement. Conversely, when the rotary ring 26 is turned in the opposite direction so as to loosen the chuck 29 and thereby release the mouthpiece 12, the cam surface 26a causes the slidable piece 30 to be displaced in the opposite direction, so that the increased diameter opening 30b moves to the center of the mouthpiece 12, allowing the latter to be withdrawn through the opening 30b.

The operating slider 28 is mounted on the unit 25 so as to be slidable along the length thereof. Intermediate its length, the slider 28 is integrally assembled with a retainer 31 which is adapted to hold the rod-shaped projection 16 of the fixture 15 in a detachable manner. The retainer 31 includes a cylindrical casing 32 secured to the slider 28 and extending in a direction orthogonal to the direction of sliding movement of the slider 28. A piston-shaped lock 33 is slidably fitted in the casing 32 while a coiled spring 34 urges the lock 33 toward the projection 16. The lock 33 is integrally formed with an operating button 35 opposite the spring 34 and projects out of the casing 32.

Both the casing 32 and the lock 33 are formed with openings 36, 37, respectively, which extend therethrough along the longitudinal direction of the operating unit 25, thereby allowing the rod-shaped projection 16 of the fixture 15 to be inserted therein. When the button 35 is pushed inward, the lock 33 is urged into the casing 32 until both openings 36, 37 are aligned with each other. When the button 35 is released, after insertion of the rod-shaped projection 16, the spring 34 urges the lock 33 in a direction so as to allow the projection 16 to be carried or held by the retainer 31. When the fixture 15 is assembled integrally with the slider 28, rotation of the operating unit 25 does not cause a twisting of the wire electrode 20 since the latter is freely disposed within the fixture 15. Further, detachment of the operating unit 25 and rotation of the operating pipe 14 will result in no twisting of the wire electrode 20.

Accordingly, when the mouthpiece 12 and the fixture 15 are engaged with the receiver 27 and the slider 28, respectively, of the operating unit 25 and the slider 28 is slid with respect to the operating unit 25, the wire electrode 20 may be advanced or retracted along the sheath 11 through the fixture 15, the stop 22, the pipe 43 and the retracting member 21.

It is to be noted that the wire electrode 20 is electrically connected to a socket (not shown) which is mounted on the operating slider 28, through the fixture 15 and the retainer 31. The socket is electrically connected to a high frequency generator through a cord, not shown, so as to be fed with high frequency current.

Upon operation, an endoscope is inserted into a coeloma, while the sheath 11 of the high frequency instrument having the operating unit 25 mounted thereon is inserted through a channel of the endoscope and thereby into the coeloma. When the slider 28 is moved forward with respect to the operating unit 25, both the wire electrode and the wire detent member 19 move forward. Thereby a distal end of the wire electrode 20 projects out of the free end of the sheath 11. Further movement in this forward direction causes the detent member 19 to abut against the detent ring 23 where the forward movement is stopped.

Figure 6:
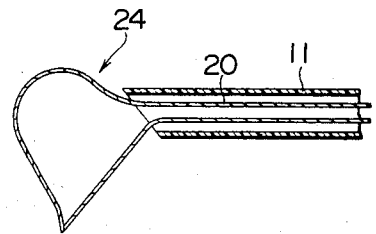
FIG. 6 is an enlarged section of a semi-circular loop which is formed by a portion of a wire electrode which extends out of the free end of a sheath.

As the wire electrode 20 moves forward through the opening 18, a semi-circular loop 24 is formed at the distal end thereof (see FIG. 6). The loop 24 may be placed at a desired location within the coeloma, for example, around a polyp. Such condition may be observed through the endoscope, and after confirming that the loop is positively engaged with the polyp, the slider 28 may be retracted with respect to the operating unit 25, whereupon the loop 24 is closed. As the wire electrode 20 is retracted into the sheath 11, the neck of the polyp can be tightly bound. High frequency current may then be passed through the electrode while continuing the retracting movement of the slider 28 until the retracting member 21 abuts against the wire detent member 19. The detent member 19 is then further retracted, whereby the wire electrode 20 may be withdrawn into the free end of the sheath 11 thus achieving an excision of the polyp.

It will be understood that the operating unit 25 is rotatable relative to the sheath 11 and the wire electrode 20. Further, if the operating unit 25 is detached, and the operating pipe 14 is intentionally twisted, such twist will not be transmitted to the sheath 11 or to the wire electrode 20 since the stop 22, which is secured to the pipe 43 and which is located at the proximate end of the wire electrode 20, is spaced apart from the fixture 15. spaced apart. Accordingly, any rotation of the operating unit 25 and the operating pipe 14 cannot cause an entangling of the semi-circular loop 24 extending from the wire electrode 20, nor cause a seizing of the loop by the polyp.

Figure 7:
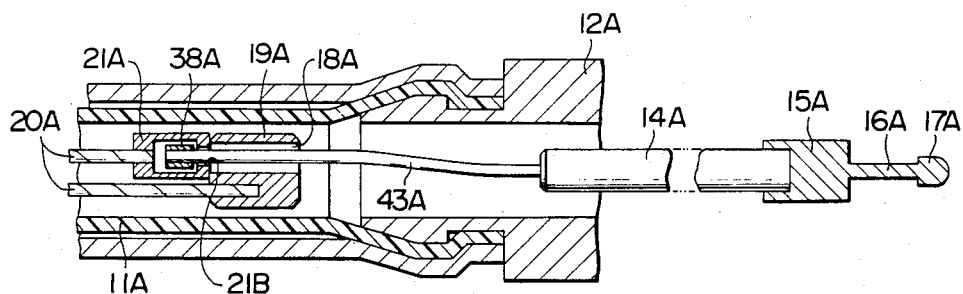
FIG. 7 is an enlarged longitudinal section of part of a high frequency instrument for incision and excision according to another embodiment of the invention.

FIG. 7 is an enlarged view, showing an essential portion of an alternate embodiment of the present invention. A fixture 15A includes a rod-shaped projection 16A and a stop 17A. An operating pipe 14A has its outer end secured to the fixture 15A while its inner end has a reduced diameter pipe 43A secured therein. The pipe 43A extends through a mouthpiece 12A and has its inner end operatively connected to a retracting member 21A, which is adapted to abut against a wire detent member 19A associated with the sheath 11A. The retracting member 21A is in the form of a bag having an opening 21B in its rear wall, through which the pipe 43A extends into the hollow interior of the retracting member 21A. One end of a wire electrode 20A is secured to the front wall of the retracting member 21A. An annular stop member 38A, having a greater diameter than opening 21B, is secured around the portion of inner end of pipe 43A which is disposed within the hollow interior of the retracting member 21A. Accordingly, the stop 38A and the pipe 43A are rotatable relative to the retracting member 21A, and are operatively connected thereto only when the wire electrode is advanced and retracted. The inner end portion of the pipe 43A extends through an opening 18A is formed in a wire detent member 19A before entering the retracting member 21A. The other end of the wire electrode 20A is secured to the detent member 19A itself. In other respects, the arrangement is similar to that of the previous embodiment, and hence will not be described. The high frequency instrument of this embodiment operates in a similar manner as the previous embodiment shown in FIGS. 3 to 6. Therefore, if an operating unit 25 or the operating pipe 14A are rotated, the rotation will not be transmitted to the wire electrode 20A since the wire electrode 20A is operatively separate from the operating pipe 14A and the pipe 43A. Accordingly, there is no entangling of a semi-circular loop formed at the distal end of the wire electrode 20A, with the tissue of an affected part.

Figure 8:
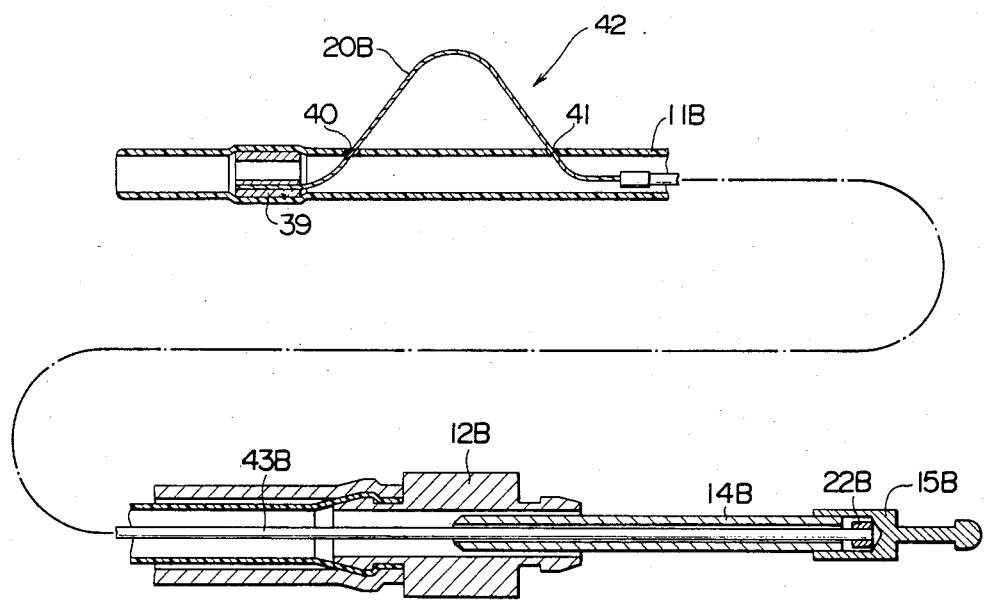
FIG. 8 is an enlarged longitudinal section of part of a high frequency instrument for incision and excision according to a further embodiment of the invention.

FIG. 8 shows a further embodiment of the invention which illustrates the invention as applied to a high frequency treatment instrument commonly referred to as a high frequency knife. The high frequency knife includes a wire electrode 20B having one end secured to an anchorage 39 which is mounted inside a sheath 11B adjacent to the inner end thereof. The other end of the electrode 20B is secured to a stop 22B which is disposed in the internal space within fixture 15B. The wire electrode 20B extends through an opening 40 formed in the sidewall of the sheath 11B and is then passed back through an opening 41 also formed in the sidewall of the sheath 11B and thereafter extending through operating pipe 14B. The stop 22B is secured to that end of the pipe 43B which is disposed within that hollow interior of the fixture 15B after having been passed through the sheath 11B, a mouthpiece 12B and an operating pipe 14B. That portion of the wire electrode 20B which extends externally of the sheath 11B is adapted to form a knife 42. This embodiment differs from the previous embodiment in that the detent member 19 or 19A and the detent ring 23 are eliminated, but in other respects, the arrangement is similar to the embodiments shown in FIGS. 3 and 7.

In operation, when a slider 28 on an operating unit 25 or the operating pipe 14B is moved in the forward direction, the wire electrode 20B is advanced also, whereby the knife 42, defined by the wire electrode 20B which is located externally of the sheath 11B, projects laterally to form a loop which is used to surround the tissue of an affected part. As the wire electrode 20B is retracted, the knife 42 moves toward the sheath, reducing its size. Passage of high frequency current allows the tissue of an affected part to be treated. The high frequency knife of this embodiment is suitable for use in the incision of the nipple of duodenum, for example. As before, a rotation of the operating unit or an intentional rotation of the operating pipe cannot cause a twisting of the wire electrode, thus preventing the knife formed from entangling with the nipple as during the incision thereof.

What is claimed is:
1. An instrument for use with a source of high frequency power for incision and excision of affected tissue, said instrument comprising:
 a sheath formed by a pipe of flexible, electrically insulating material and having a substantial length;
 a wire electrode disposed within said sheath so as to be freely movable therein between a first position wherein said wire electrode is wholly within said sheath and a second position wherein said wire electrode extends outside said sheath and forms a loop which can be passed over an affected part;
 an operating pipe means disposed for movement into and out of said sheath through an opening formed in said sheath at a proximate end of the sheath and for causing an advancing and retracting movement of said wire electrode; and
 an operating unit including a slider connected to said operating pipe which permits an operator to cause advancing and retracting movement of said pipe, said operating pipe being rotatable relative to said wire electrode.

2. A high frequency instrument for incision and excision according to claim 1, in which said operating pipe is connected to said slider by a fixture which is integrally mounted on said operating pipe and surrounds one end of said wire electrode, said fixture being rotatable relative to said one end of said wire electrode.

3. A high frequency instrument for incision and excision according to claim 1, in which a portion of said wire electrode extends through said proximate opening of said sheath and through said operating pipe into an internal space within a fixture secured to said pipe, said wire end being locked against disengagement from said fixture by means of a stop disposed in said space.

4. A high frequency instrument for incision and excision according to claim 1, in which said operating pipe is disposed in surrounding relationship to said wire electrode.

5. A high frequency instrument for incision and excision according to claim 1, wherein said operating pipe is also rotatable relative to said operating unit.

6. A high frequency instrument for incision and excision according to claim 5, wherein said operating pipe is rotatable relative to said slider.

7. A high frequency instrument for incision and excision according to claim 1, further including a wire detent member having one end of said wire electrode securely attached thereto and through which an opposite end of said wire electrode slidably passes and further including a retracting member mounted on said wire electrode and operating as a stop to limit the movement of said wire electrode through said wire detent member.

8. A high frequency instrument for incision and excision according to claim 1, further including a wire detent member having one end of said wire electrode securely attached thereto, said operating pipe passing through an opening in said wire detent member and being rotatably coupled to an opposite end of said wire electrode.

9. A high frequency instrument for incision and excision according to claim 8, further including a retracting member coupled to said other end of said wire electrode, said operating pipe being rotatably coupled to said retracting member, said retracting member being of a size and shape which prevents it from passing through said opening in said wire detent member.

10. A high frequency instrument for incision and excision according to claim 9, wherein said operating pipe includes a reduced diameter section which passes through said opening in said wire detent member and extends into an internal space of said retracting member.

11. A high frequency instrument for incision and excision according to claim 9, further including a stop member coupled to said reduced diameter section of said pipe at a location within said internal space of said retracting member and preventing said pipe from being removed from said retracting member.

* * * * *